(12) United States Patent
Ruffner et al.

(10) Patent No.: US 6,307,041 B1
(45) Date of Patent: Oct. 23, 2001

(54) CIRCULAR, HAIRPIN, CIRCULAR/HAIRPIN, LARIAT, AND HAIRPIN-LARIAT HAMMERHEAD RIBOZYMES

(75) Inventors: Duane E. Ruffner; Laixin Wang, both of Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 09/647,314

(22) PCT Filed: Mar. 29, 1999

(86) PCT No.: PCT/US99/06770

§ 371 Date: Dec. 6, 2000

§ 102(e) Date: Dec. 6, 2000

(87) PCT Pub. No.: WO99/50277

PCT Pub. Date: Oct. 7, 1999

Related U.S. Application Data

(60) Provisional application No. 60/079,791, filed on Mar. 28, 1998.

(51) Int. Cl.$^7$ ................................................ C07H 21/04
(52) U.S. Cl. ................. 536/24.5; 536/23.1; 536/23.2; 536/24.3
(58) Field of Search .................. 536/23.1, 23.2, 536/24.5, 24.3; 435/91.31, 375; 514/44

(56) References Cited

U.S. PATENT DOCUMENTS 5,652,094   7/1997   Usman et al. ................. 536/24.5
6,096,880 * 8/2000   Kool ................................. 536/25.3

OTHER PUBLICATIONS

Wang et al. Rational Design of a New Hammerhead Ribozyme Configuration: Lariat Hammerhead Ribozymes as Improved Antisense Therapeutics. J. Am. Chem. Soc. 1998, vol. 120, No. 31, pp. 7684–7690.

Wang et al. Novel Configurations of the Hammerhead Ribozyme: Increased Activity and Reduced Magnesium Ion Requirement. Biochemical and Biophysical Res. Com., Sep. 1998, vol. 150, No. 3, p. 711–719.

Wang et al. Oligoribonucleotide circularization by 'template–mediated' ligation with T4 RNA ligase: synthesis of circular hammerhead ribozymes. May 15, 1998, vol. 26, No. 10, pp. 2502–2504. Nucleic Acids Res.

Puttaraju et al. Circular ribozymes generated in *Escherichia coli* using Group 1 self–splicing permuted intron–exon sequences. The Journal of Biological chemistry. Oct. 18, 1996, vol. 271, No. 42, p. 26081–26087.

* cited by examiner

*Primary Examiner*—John L. LeGuyader
*Assistant Examiner*—Janet Epps
(74) *Attorney, Agent, or Firm*—Clayton, Howarth & Cannon, P.C.

(57) ABSTRACT

Hammerhead ribozyme derivatives termed circular, hairpin, circular/hairpin, lariat, and hairpin-lariat ribozymes are disclosed. These hammerhead ribozyme derivatives are catalytically active and have increased specific activity and reduced requirement for divalent metal ion co-factor as compared to wild type hammerhead ribozyme.

19 Claims, 9 Drawing Sheets

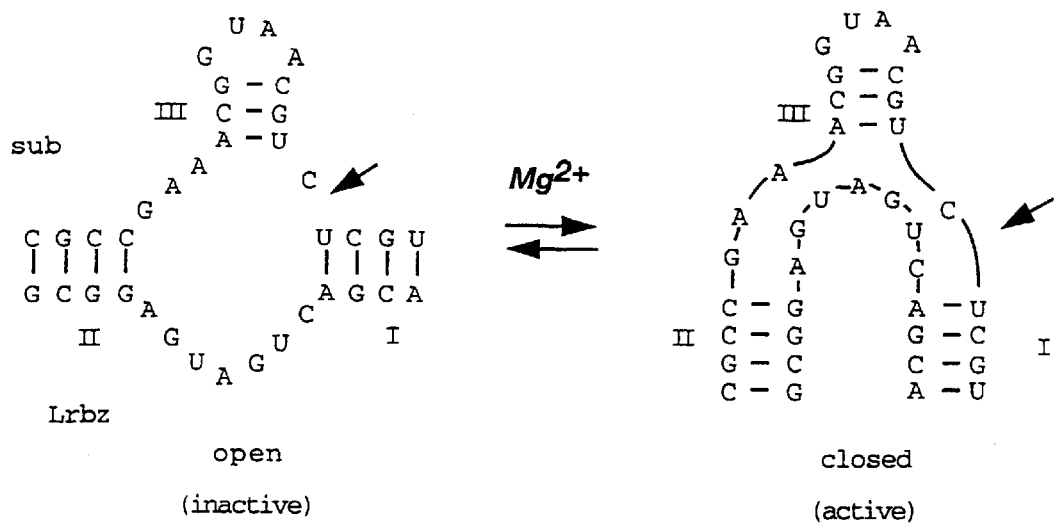
*Fig. 1A*
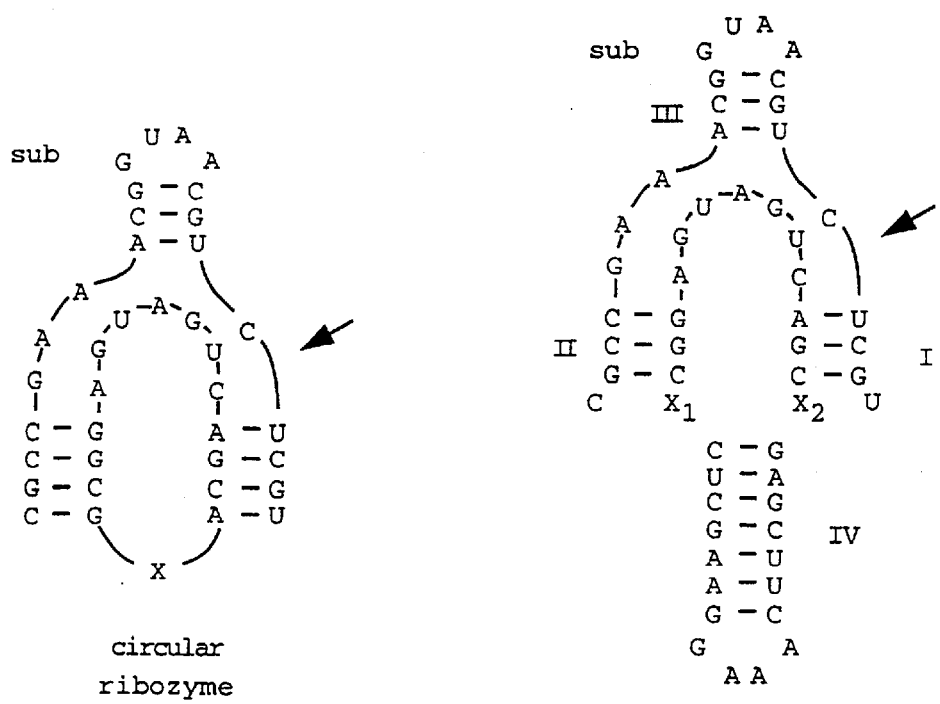
*Fig. 1B*
*Fig. 1C*

Circular rbz3 (Crbz3)

Crbz3L18: x=linker 18
Crbz3L27: x=linker 27

Linear rbz (Lrbz3)

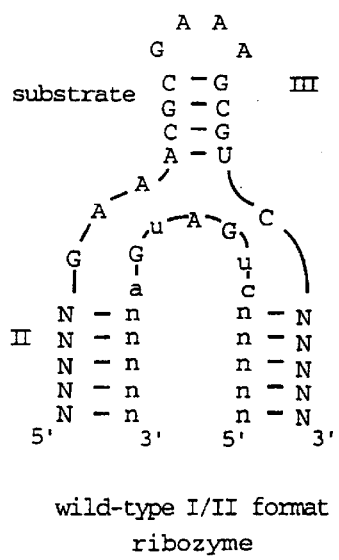
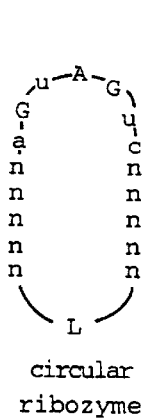
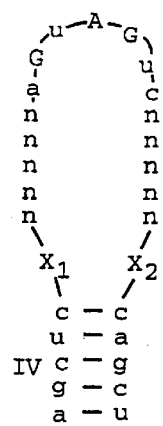
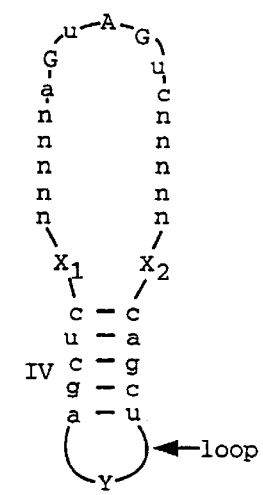
wild-type I/II format ribozyme
Fig. 8A
circular ribozyme
Fig. 8B
hairpin ribozyme
Fig. 8C
circular/hairpin ribozyme
Fig. 8D
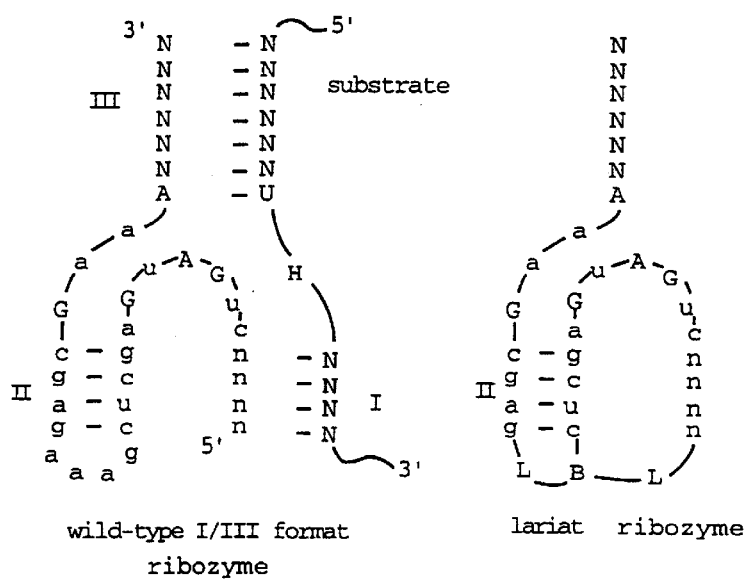
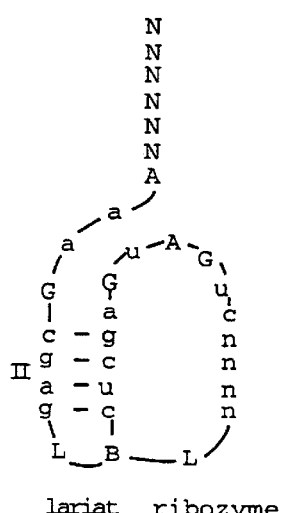
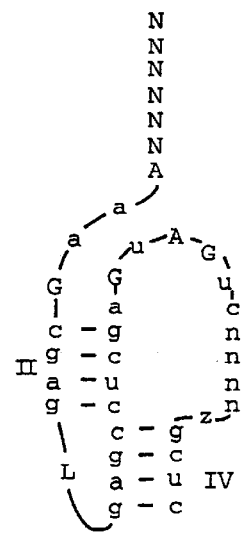
wild-type I/III format ribozyme
Fig. 8E
lariat ribozyme
Fig. 8F
hairpin/lariat ribozyme
Fig. 8G

CIRCULAR, HAIRPIN, CIRCULAR/HAIRPIN, LARIAT, AND HAIRPIN-LARIAT HAMMERHEAD RIBOZYMES

This is a 371 application of PCT/US99/06770 filed Mar. 29, 1999, which claims the benefit of provisional application No. 60/079,791 filed Mar. 28, 1998.

BACKGROUND OF THE INVENTION

This invention relates to zibozymes. More particularly, the invention relates to derivatives of wild type hammerhead ribozymes, termed circular, hairpin, circular/hairpin, lariat, and hairpin/lariat hammerhead ribozymes.

Ribozymes are RNA or modified RNA molcules that can cleave themselves or other nucleic acid molecules (usually RNA) in a catalytic fashion, similar to traditional protein enzymes. The hammerhead ribozyme is one of the smallest ribozymes currently known, and therefore is the most studied of catalytic RNAs. It has shown great utility as a research tool and an antisense therapeutic composition (e.g., U.S. Pat. No. 5,254,678).

The structure and mechanism of the hammerhead ribozyme have been examined using a broad range of approaches. Recently, crystal structures of the hammerhead have been reported. The crystal structures exhibit a Y-shaped configuration for the hammerhead. In this configuration helices I and II form the adjacent upper arms, while helix III forms the lower leg of the Y. Based on these findings, hammerheads in which helix I and II are constrained to remain adjacent and roughly parallel, are expected to be catalytically active. See Sigurdsson, S. T., Tuschl, T., and Eckstein, F. (1995) RNA 1, 575–83.

The metal dependence of folding and cleavage of the hammerhead domain have been examined by several groups using a variety of techniques (Amiri, K. M., and Hagerman, P. J. (1996) J. Mol. Biol. 261, 125–34; Bassi, G. S., Murchie, A. I. H., and lilley, D. M. J. (1996) RNA 2, 756–768; Heus, H. A., and Pardi, A. (1991) J. Mol. Biol. 217, 113–24; Menger, M., Tuschl, T., Eckstein, F., and Porschke, D. (1996) Biochemistry 35, 14710–6; Olita, M., Vinayak, R., Andrus, A., Takagi, Y., Chiba, A., Kaniwa, H., Nishikawa, F., Nishikawa, S., and Taira, K. (1995) Nucleic Acids Symp. Ser. 34, 219–20; Orita, M., Vinayak, R., Andrus, A., Warashina, M., Chiba, A., Kaniwa, H., Nishikawa, F., Nishikawa, S., and Taira, K. (1996) J. Biol. Chem. 271, 9447–54; Simorre, J. P., Iegault, P., Hangar, A. B., Michiels, P., and Pardi, A. (1997) Biochemistry 36, 518–25). These studies indicate that divalent metal ions induce a structural transition, and this coincides with the activation of the hammerhead. Based on these findings, it is believed that an inactive or open conformation is first formed on substrate binding. Subsequently, metal ion addition induces a conformational change to a closed, and catalytically active structure (FIG. 1A). Crystallographic evidence (Scott, W. G., Finch, J. T., and Klug, A. (1995) Cell 81, 991–1002; Scott, W. G., Murray, J. B., Arnold, J.R.P., Stoddard, B. L., and Klug, A. (1996) Science 274, 2065–9; Pley, H. W., Flaherty, K. M., and McKay, D. B. (1994) Nature 372, 68–74), and gel shift (Bassi, G. S., Mollegaard, N. E., Murchie, A. I., von Kitzing, E., and ailley, D. M. (1995) Nat. Struct. Biol. 2, 45–55) and fluorescence resonance energy transfer (FRET) analysis (Tuschl, T., Gohlke, C., Jovin, T. M., Westhof, E., and Eckstein, F. (1994) Science 266, 785–9) all support a Y-shaped structure for the closed and active conformation. In this conformation, helices I and II are adjacent and represent the two arms of the Y, while helix III forms the leg (FIG. 1A).

For use of ribozymes in research and especially in therapeutic treatment of various diseases and conditions by antisense-mediated gene inhibition, it would be advantageous to develop hammerhead ribozyme derivatives that have a higher specific activity, have a reduced requirement for magnesium ions, and are more resistant to nuclease degradation than wild-type hammerhead ribozymes.

In view of the foregoing, it will be appreciated that providing hammerhead ribozyme derivatives with these desirable properties would be a significant advancement in the art.

BRIEF SUMMARY OF THE INVENTION

It is an object of the present invention to provide derivatives of hammerhead ribozymes that have an increased specific activity and resistance to nuclease degradation and a reduced dependence on metal ion co-factors.

It is another object of the invention to provide a method of using such hammerhead ribozyme derivatives for antisense-mediated gene inhibition.

These and other objects can be addressed by providing a hammerhead ribozyme derivative having a structure represented by:

$$(L)_b\text{—}R^1\text{-(cugauga)-}R^2$$

wherein $R^1$ and $R^2$ are oligoribonucleotides of at least 2 bases configured for base pairing with a substrate; L is a spacer; and b is 0 or 1, with the proviso that if b is 0, then $R^1$ and $R^2$ are bonded together with a phosphodiester bond, and if b is 1, then L is covalently bonded to $R^2$.

Another embodiment of the invention comprises a hammerhead ribozyme derivative having a structure represented by:

$$R^3\text{—}(L^1)_b\text{—}R^1\text{-(cugauga)-}R^2\text{—}(L^2)_d\text{—}R^4$$

wherein $R^1$ and $R^2$ are oligoribonucleotides of at least 2 bases configured for base pairing with a substrate; $R^3$ and $R^4$ are oligonucleotides of at least 2 bases configured for base pairing with each other; $L^1$ and $L^2$ are spacers; and b and d are 0 or 1.

Another embodiment of the invention comprises a hammerhead ribozyme derivative having a structure represented by:

$$R^3\text{—}(L^1)_b\text{—}R^1\text{-(cugauga)-}R^2\text{—}(L^2)_d\text{—}R^4\text{—}(L^3)_f$$

wherein $R^1$ and $R^2$ are oligoribonucleotides of at least 2 bases configured for base pairing with a substrate; $R^3$ and $R^4$ are oligonucleotides of at least 2 bases configured for base pairing with each other, $L^1$, $L^2$, and $L^3$ are spacers; and b, d, and f are 0 or 1, with the proviso that if f is 0, then $R^3$ and $R^4$ are bonded together by a phosphodiester bond, and if f is 1, then $L^3$ is bonded to both $R^3$ and $R^4$.

Still another embodiment of the invention comprises a hammerhead ribozyme derivative having a structure represented by:

$$(L^1)_b\text{—}R^1\text{-(cugauga)-}R^2\text{—}Q\text{—}(L^2)_d\text{—}R^4$$

wherein $R^1$ is an oligoribonucleotide of at least 2 bases configured for base pairing with a substrate; $R^2$ is an oligoribonucleotide of at least 2 bases configured for base pairing with $R^4$; $R^4$ is an oligonucleotide of at least 2 bases configured for base pairing with $R^2$; $L^1$ and $L^2$ are spacers; Q is a branching moiety; and b and d are 0 or 1, with the proviso that is b is 0, then $R^1$ is covalently bonded to Q, and if b is 1, then $L^1$ is covalently bonded to Q.

Yet another embodiment of the invention comprises a hammerhead ribozyme derivative having a structure represented by:

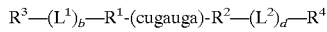

$R^3$—$(L^1)_b$—$R^1$-(cugauga)-$R^2$—$(L^2)_d$—$R^4$ wherein $R^1$ is an oligoribonucleotide of at least 2 bases configured for base pairing with a substrate, $R^2$ is an oligoribonucleotide of at least 2 bases configured for base pairing with both $R^3$ and $R^4$; $R^3$ is an oligonucleotide of at least 2 bases configured for base pairing with $R^2$; $L^1$ and $L^2$ are spacers; and b and d are 0 or 1.

In all of these embodiments the spacers can be independently selected from the group consisting of ribonucleotides, oligoribonucleotides, —O—$CH_2CH_2CH_2O$—, —O—$(CH_2CH_2O)_3$—, —O—$(CH_2CH_2O)_6$—, —O—$(CH_2CH_2O)_3$—$OPO_3$—O—$(CH_2CH_2O)_6$—, and —O—$(CH_2CH_2O)_6$—$OPO_3$—O—$(CH_2CH_2O)_6$—.

Yet another embodiment of the invention comprises a hammerhead ribozyme derivative having a structure selected from the group consisting of circular ribozymes, hairpin ribozymes, circular/hairpin ribozymes, lariat ribozymes, and hairpin-lariat ribozymes.

A method of using a hammerhead ribozyme having a structure selected from the group consisting of circular ribozymes, hairpin ribozymes, circular/hairpin ribozymes, lariat ribozymes, and hairpin-lariat ribozymes comprises contacting a hammerhead ribozyme substrate with said hammerhead ribozyme under conditions configured for digestion of said substrate.

BRIEF DESCRIPTION OF TBE SEVERAL VIEWS OF THE DRAWINGS

FIG. 1A shows open (inactive) and closed (active) conformations of the hammerhead ribozyme formed between a linear substrate (sub; SEQ ID NO:1) and a linear ribozyme (Lrbz; SEQ ID NO:2); helices I, II, and III are marked, and the arrow indicates the cleavage site.

FIG. 1B shows a ribozyme formed between a linear substrate (sub; SEQ ID NO:1) and a covalently closed circular ribozyme (e.g., SEQ ID NO:2; SEQ ID NO:3); the arrow indicates the cleavage site, and X is a linker.

FIG. 1C shows a ribozyme formed between a linear substrate (sub; SEQ ID NO:1) and a covalently closed circular/hairpin ribozyme (e.g., SEQ ID NO:4–8); the arrow indicates the cleavage site, and $X_1$ and $X_2$ are linkers.

Figure 3A:
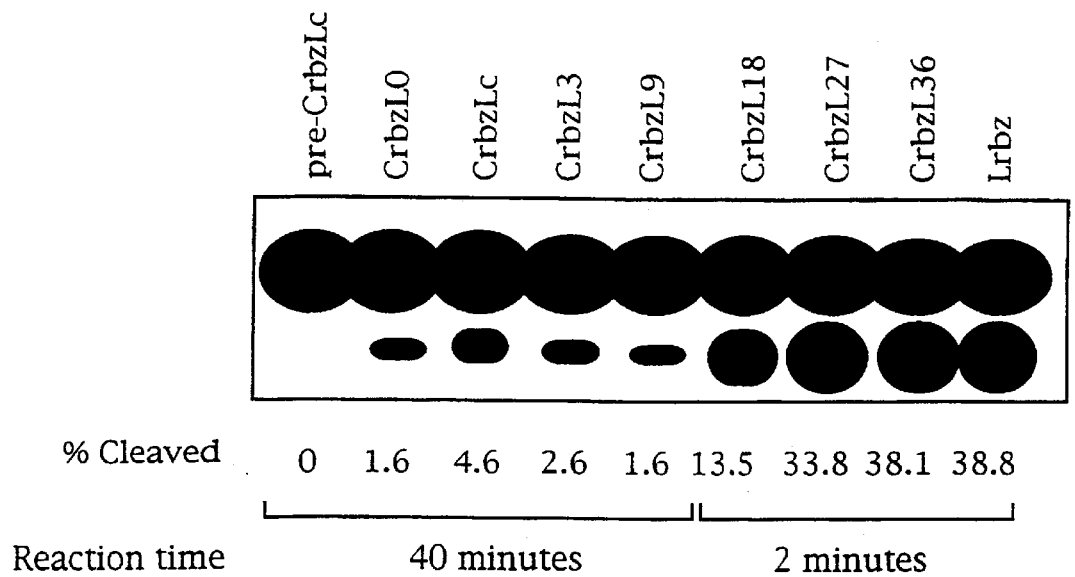
FIG. 3A shows cleavage of a substrate (sub) by linear and circular ribozymes; each lane contains the cleavage reaction for the ribozyme indicated, and pre-CrbzLc indicates the cleavage reaction for the linear precursor to CrbzLc.
Figure 3B:
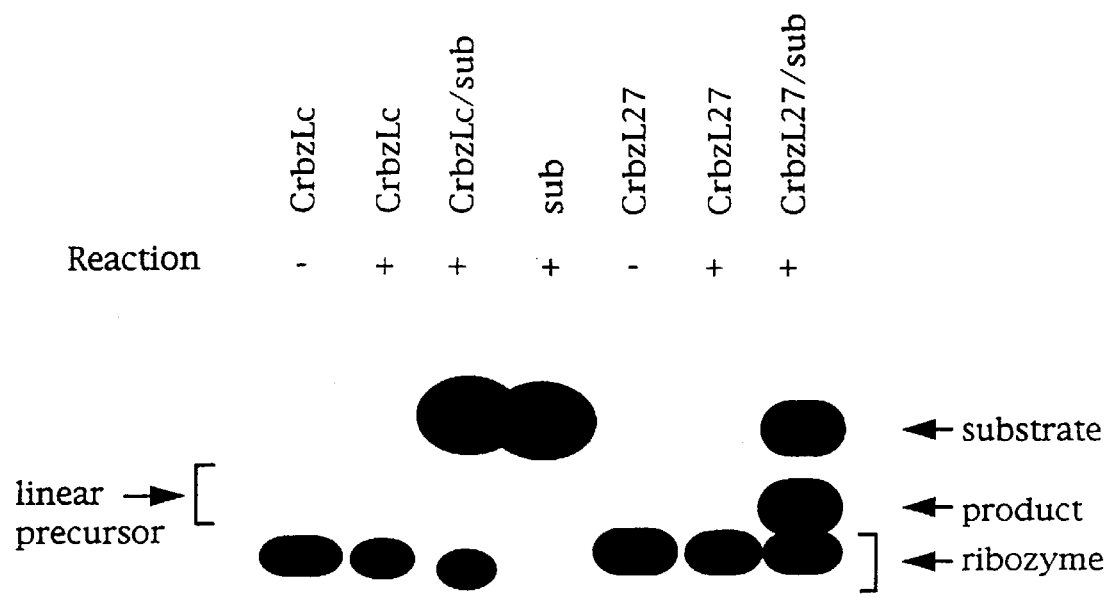

FIG. 3B shows cleavage reactions for linear contaminants; the ribozymes and substrate, as indicated, were incubated under similar conditions used in the cleavage reactions (lanes marked +). As controls, unreacted CrbzLc and CrbzL27 were loaded directly on the gel in lanes designated (–). The positions of the substrate, ribozymes, and cleavage product are indicated by the arrows. "Linear precursor" indicates the position where the linear precursors migrate on the gel and where the nicked circles would appear.

Figure 4A:
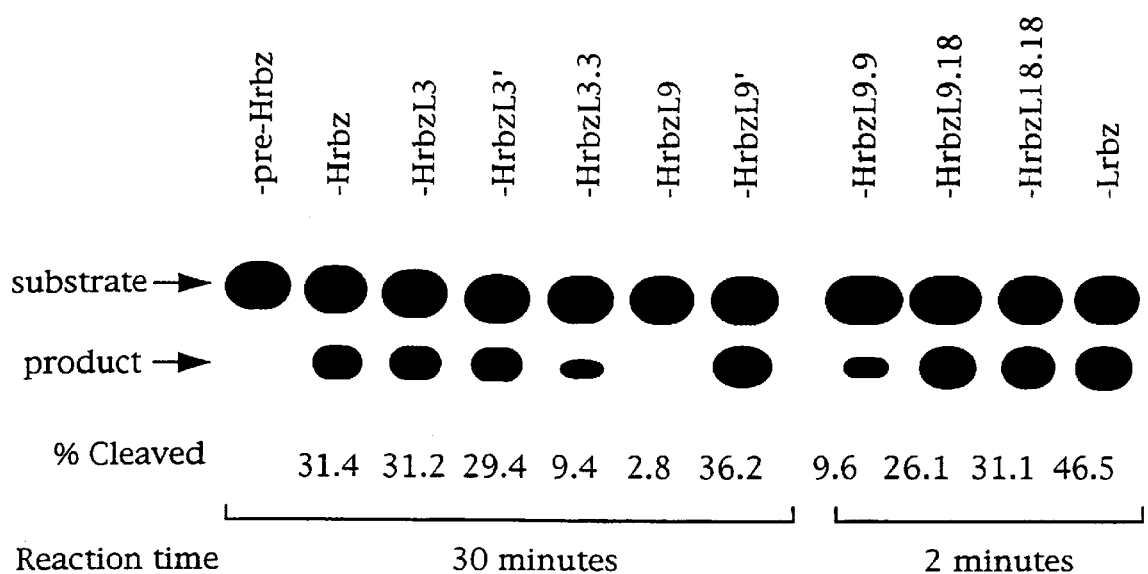
Figure 4B:
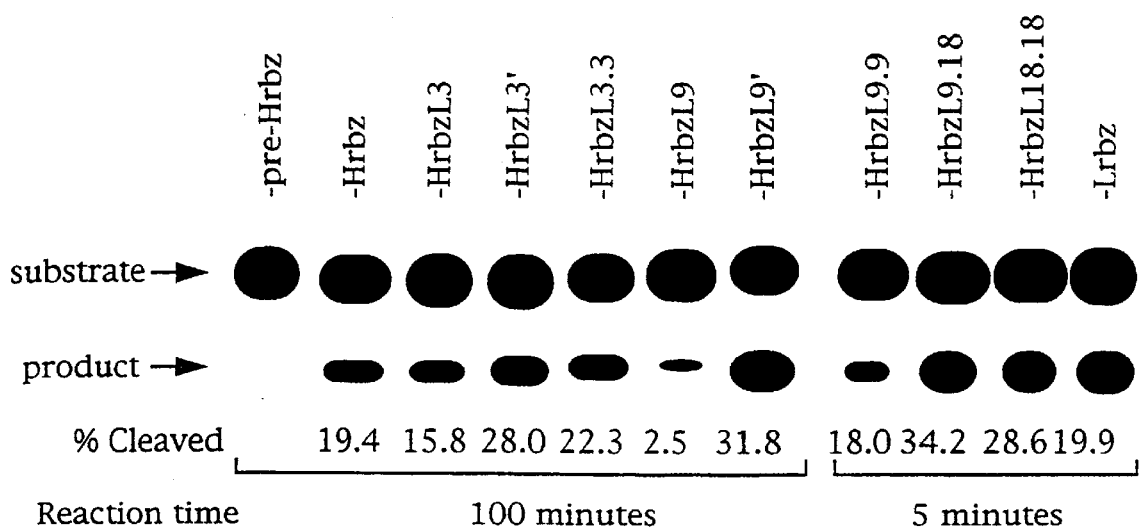

FIGS. 4A and 4B show cleavage reactions of the linear and circular/hairpin ribozymes against substrates sub and sub2, respectively. The conditions of the cleavage reactions were the same as for the circular ribozymes, except the reaction times differed as indicated. Each lane contains the cleavage reaction for the ribozyme indicated. "Pre-Hrbz" indicates the cleavage reaction for the linear precursor to Hrbz.

Figure 5A:
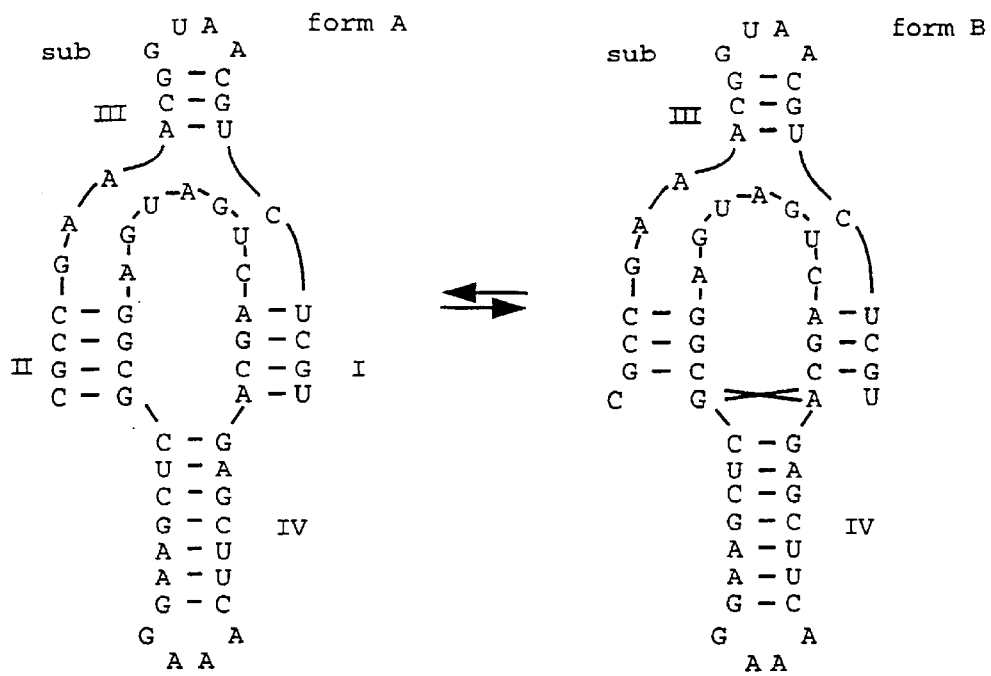
Figure 5B:
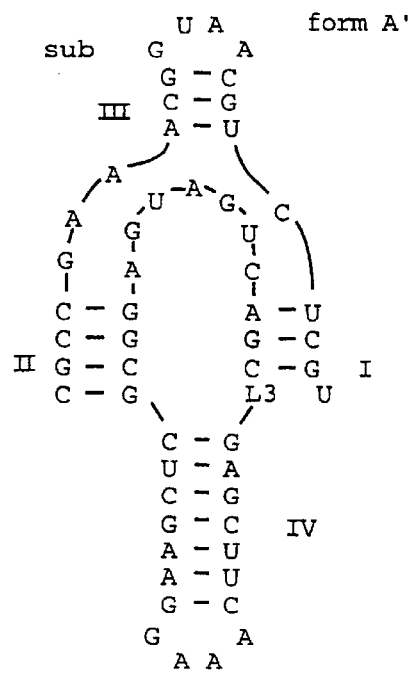
Figure 5C:
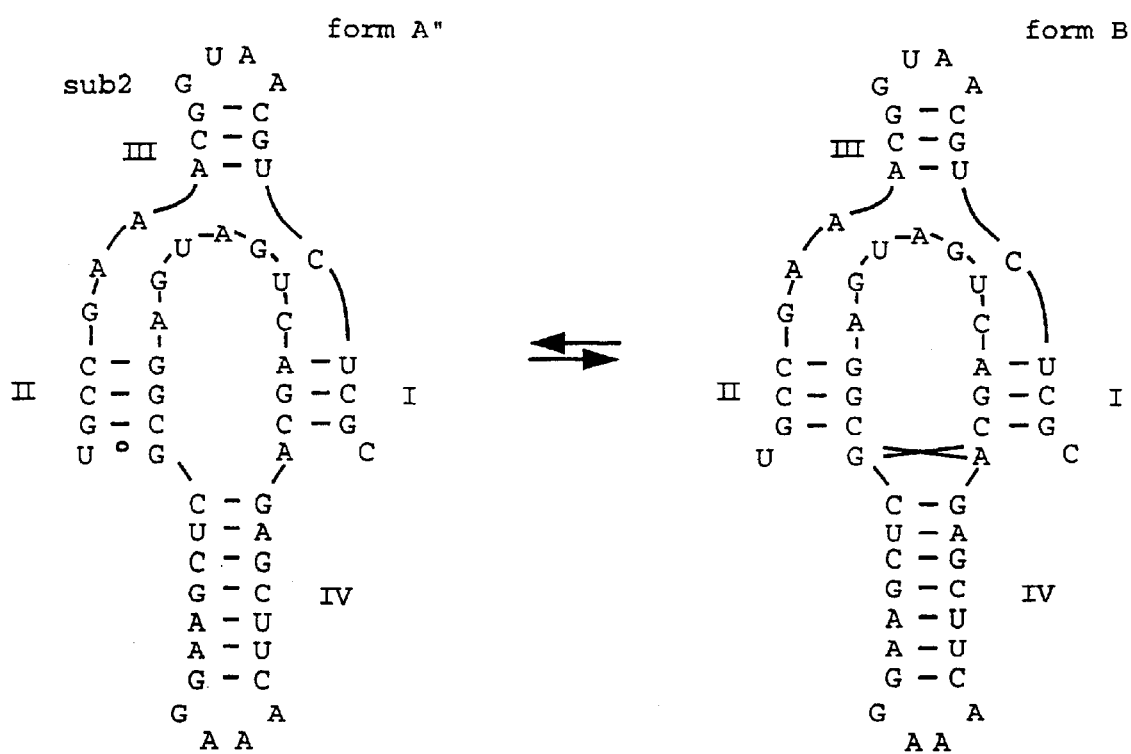

FIGS. 5A, 5B, and 5C show possible base-pairing configurations for the complex between (A) the substrate, sub, and the circular/hairpin ribozyme Hrbz, (B) the substrate, sub, and the circular/hairpin ribozyme HrbzL3', and (C) the substrate, sub2 (SEQ ID NO:11), and Hrbz.

Figure 6B:
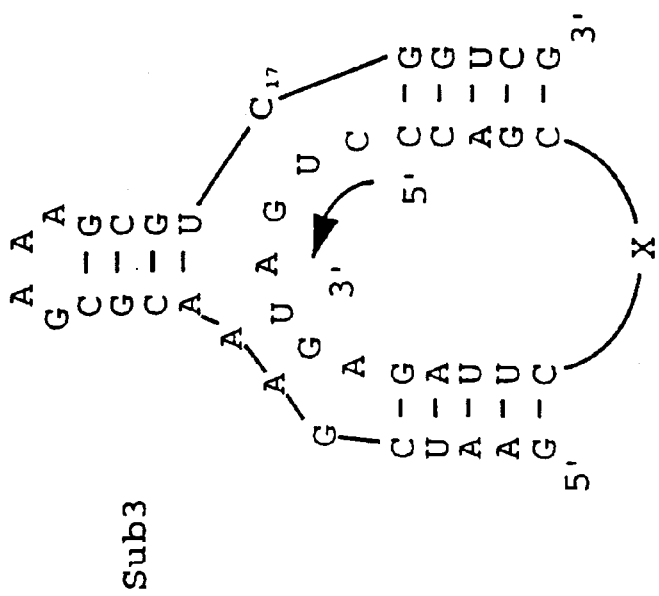
Figure 6A:
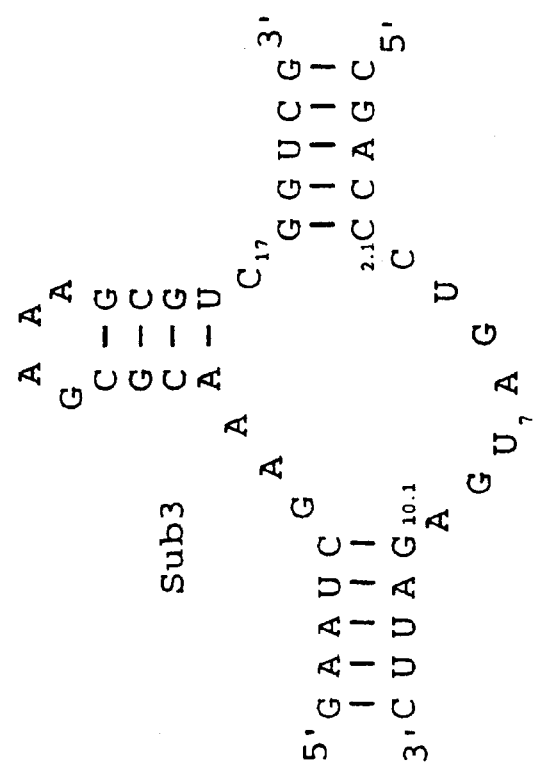

FIGS. 6A and 6B show linear (A) and circular (B) ribozymes used for kinetic analysis: (A) substrate, subs (SEQ ID NO:12), and linear ribozyme, Lrbz3; (B) substrate, sub3, and circular tibozyme, Crbz3.

Figure 7:
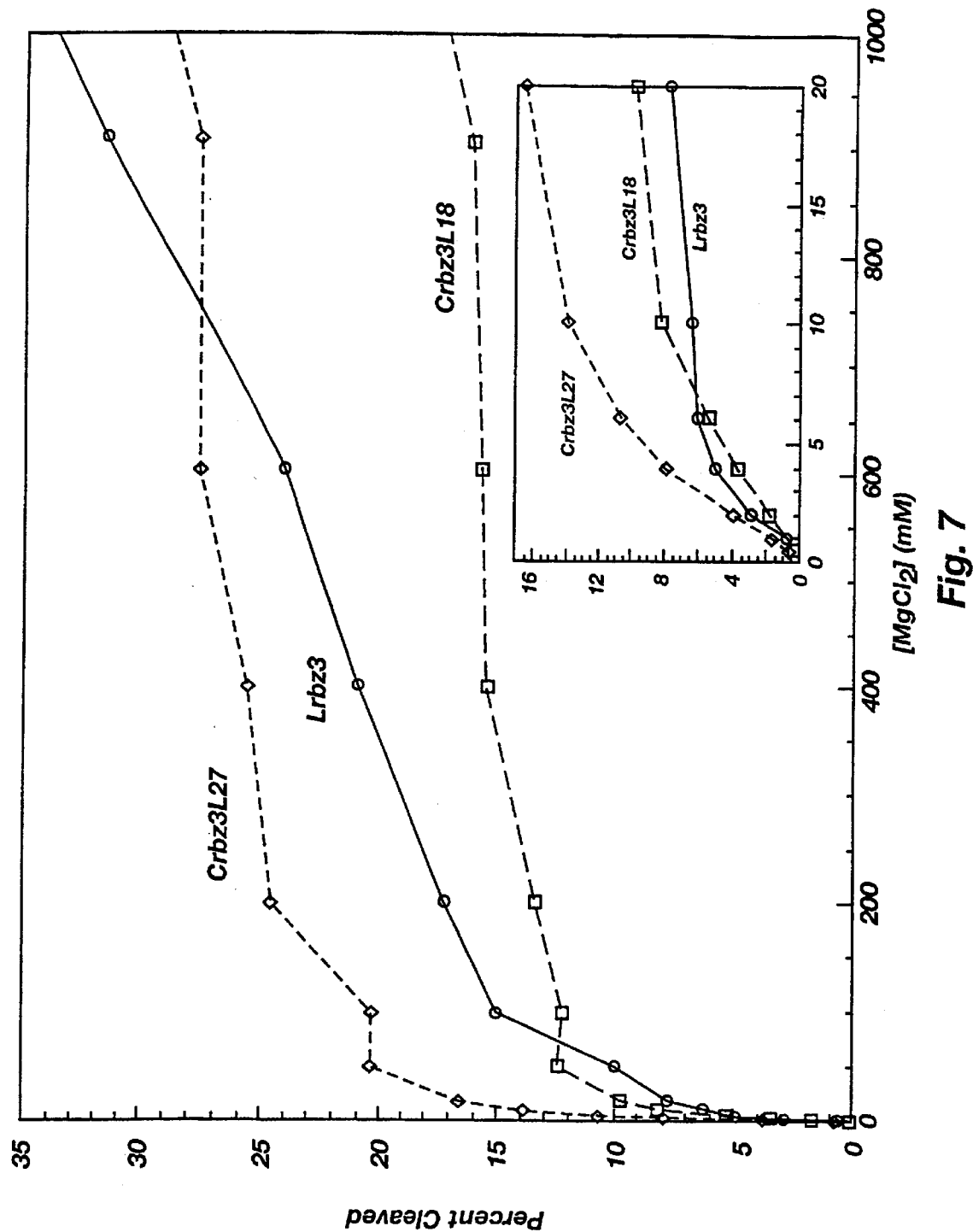

FIG. 7 shows magnesium ion dependence of cleavage of linear and circular ribozymes: (◇) Crbz3L27, (○) Lrbz3, (□) Crbz3L18.

FIGS. 8A–G show: (A) wild-type I/II format ribozyme (SEQ ID NO:13) and substrate (SEQ ID NO:14); (B) an illustrative circular ribozyme (SEQ ID NO:13) according to the present invention; (C) an illustrative hairpin ribozyme (SEQ ID NO:13) according to the present invention; (D) an illustrative circular/hairpin ribozyme (SEQ ID NO:13) according to the present invention; (E) wild-type I/III format ribozyme (SEQ ID NO:15) and substrate (SEQ ID NO:16); (F) an illustrative lariat ribozyme according to the present invention; (G) an illustrative hairpin-lariat/ribozyme (SEQ ID NO:17 and SEQ ID NO:18) according to the present invention.

DETAILED DESCRIPTION

Before the present hammerhead ribozyme derivatives are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise.

In describing and claiming the present invention, the following terminology will be used in accordance with the definitions set out herein.

Five types of hammerhead ribozyme derivatives are disclosed herein: circular, hairpin, circular/hairpin, lariat, and hairpin/lariat (FIGS. 8B–D, F, G). These configurations of the hammerhead are catalytically active and provide advantages not present in the wild-type hammerhead configurations. Since they can be produced by a variety of methods, including both enzymatic and/or chemical procedures, as well as by fully automated synthesis on a DNA synthesizer, the invention is not specific for any particular method of synthesis. That is, circular, hairpin, circular/hairpin, lariat, and hairpin-lariat hammerhead ribozymes synthesized by any means are included in this invention. This would also include circular, hairpin, circular/hairpin, lariat, and hairpin-lariat hammerhead ribozymes synthesized endogenously within cells using suitable gene expression systems.

The hammerhead ribozyme derivatives of the present invention offer many advantages relative to the wild-type hammerhead ribozyme, some of which are as follows. All five configurations are locked in a closed and active conformation. This may be an advantage for the study of structure and mechanism of the hammerhead ribozyme. Some of the configurations have been shown to have the advantage of increased activity and a reduced requirement for a divalent metal ion cofactor relative to the wild-type ribozymes. The increased activity and lower metal requirement offers significant advantage for use of these molecules as therapeutic agents and research tools. These new ribozymes also possess an increased resistance to degradation by nucleases relative to wild-type ribozymes, which also represents a significant advantage.

EXAMPLE 1
Preparation of RNA Substrates and Ribozymes

To examine the possibility that helix I/II constrained hammerhead ribozymes possess catalytic activity, several ribozymes of two novel configurations were designed, a circular (FIG. 1B) and a circular/hairpin configuration (FIG. 1C). All of the circular and hairpin ribozymes prepared in this example were derived from a linear I/II format hammerhead, sub/Lrbz (FIG. 1A). As such, all the circular and hairpin ribozymes shared the same linear substrate, sub.

Circular and circular/hairpin ribozymes, except CrbzLc and CrbzL0, were prepared as follows. Ten nanomole of the linear RNA precursor and 3.0 μmole of $MgCl_2$ were dissolved in 223 μl $H_2O$. This mixture was placed at 90° C. for 3 minutes and 16° C. for at least one hour. The following was added to the RNA-containing mixture: 30 μl of 10X buffer (500 mM Tris-HCl (pH 7.7), 100 mM DTT, 30 μl of 400 mg/ml PEG 8,000, 7.5 μl of 20 mM ATP and 10 μl of 20 units/μl T4 RNA ligase. The mixtures were incubated at 16° C. overnight. CrbzLc and CrbzL0 were prepared as above, except that a DNA guide (5'-gtcgctaaga cacgtgcgcc acact-tagcg ac-3', CrbzLc (SEQ ID NO:19); 5'-gtcgctaaga cacgtcgcca cacttagcga c-3', CrbzL0 (SEQ ID NO:20)) was included in each reaction at a 1.2 fold molar excess over the precursor RNA.

The oligonucleotides were precipitated from the ligation reactions with the addition of 50 μl 3.0 M sodium acetate and 920 μl cold ethanol. The crude pellet was resuspended and fractionated in 15% or 20% denaturing polyacrylamide gels. The RNA in the gel was visualized by UV shadowing, and the products were recovered by a crush and soak method. The purified RNA was dissolved in 60 μl$H_2O$, producing stock solutions of 60–70 μM. The total recovered yields were about 40% for most of the preparations.

Figure 2A:
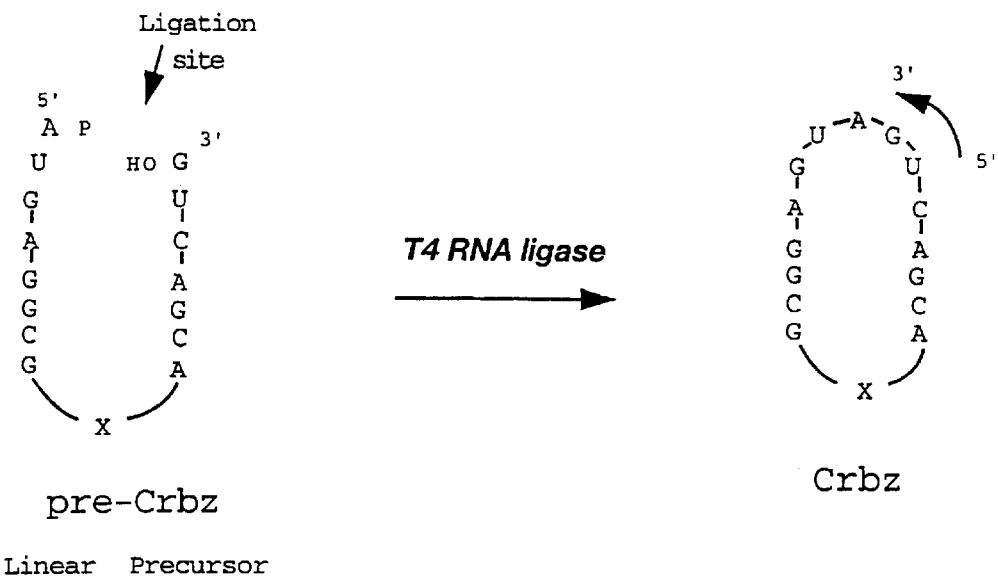
FIGS. 2A and 2B show preparation of a circular ribozyme and a circular/hairpin ribozyme, respectively, from linear precursors pre-Crbz (SEQ ID NO:9) and pre-Hrbz (SEQ ID NO:10) using T4 RNA ligase.
Figure 2B:
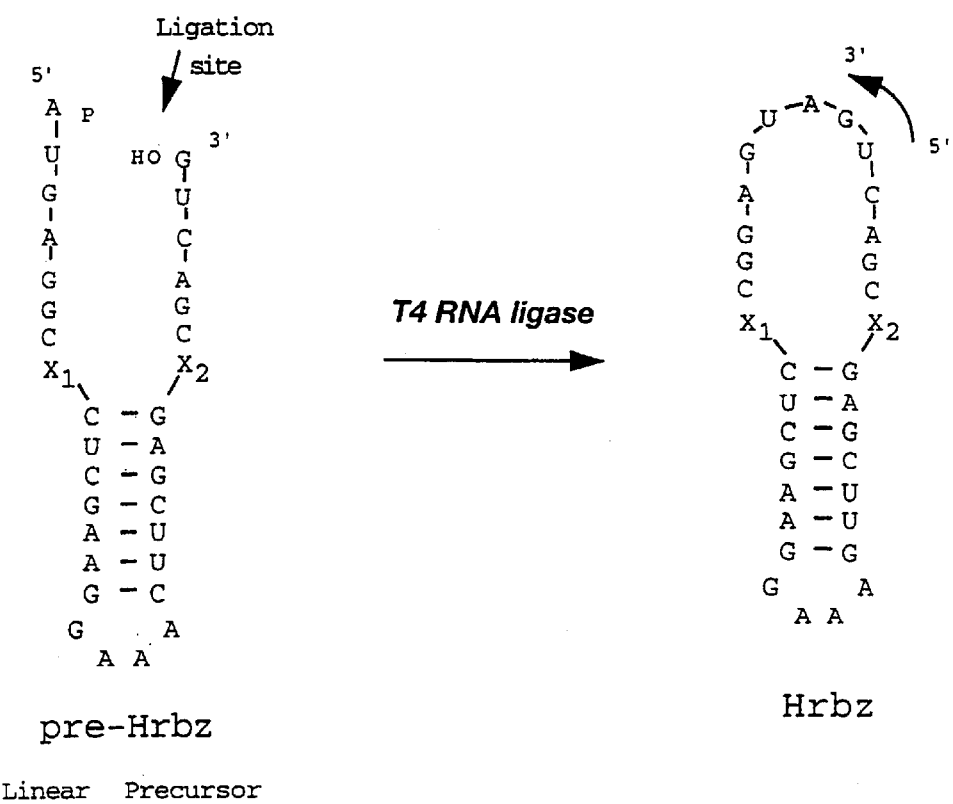

To prepare circular and hairpin ribozymes, linear RNA precursors synthesized on a DNA synthesizer, were covalently closed into circles using T4 RNA ligase (FIGS. 2A–B). Seven circular and nine hairpin ribozyme variants were examined (Tables 1 and 2), all differing in the composition of the linkers at positions X (circular), or $X_1$ and $X_2$ (hairpin). For all but CrbzLc and CrbzL0, the preferred product was the desired monomer circles or circular hairpins. At worst, the ligations produced the desired circularized product in 75% yield. More typically, yields of the desired circles were 90% or greater, linear dimers and timers were formed as minor products of ligation.

T4 RNA ligase and T4 polynucleotide kinase were from New England Biolabs. Shrimp alkaline phosphatase was from United States Biochemical. All DNA and RNA oligonucleotides were synthesized on an Applied Biosystems 394 automated DNA synthesizer on 1.0 pmole scale using the phosphoramidite method. Phosphoramidites of nucleosides, linker 3, linker 9 and linker 18 were from Glen Research; all other synthesis reagents were from Applied Biosystems. For RNA oligonucleotides that were to be circularized, a 5' phosphate was added during synthesis. DNA oligonucleotides were purified by ethanol precipitation. RNA oligonucleotides were purified by 15% or 20% denaturing polyacrylamide gel electrophoresis and recovered from the gel by a crush and soak method.

For CrbzLc and CrbzL0, the predominant product was the linear dimer, with little or no monomer circles detected. To overcome this, a guide DNA was designed to hybridize to the linear precursor RNA. The guide consisted of a hairpin closed by a loop of partial complementarity to the precursor RNA. Hybridization of the precursor RNA to the guide DNA was expected to insure that the 5' and 3' termini of the RNA were unstructured and in close proximity. In the presence of the guide sequence, CrbzLc: and CrbzL0 could be prepared in high yield with greater than 90% of the product being the desired circular monomer.

TABLE 1

Circular Ribozymes

| Name | X |
|---|---|
| CrbzLc | C (cytidine) |
| CrbzL0 | — |
| CrbzL3 | —O—$CH_2CH_2CH_2$O— |
| CrbzL9 | —O—$(CH_2CH_2O)_3$— |
| Crbz18 | —O—$(CH_2CH_2O)_6$— |
| CrbzL27 | —O—$(CH_2CH_2O)_3$—$OPO_3$—O—$(CH_2CH_2O)_6$— |
| CrbzL36 | —$(CH_2CH_2O)_6$—$OPO_3$—O—$(CH_2CH_2O)_6$— |

TABLE 2

Circular/Hairpin Ribozymes

| Name | $X_1$ | $X_2$ |
|---|---|---|
| HrbzL3 | —O—$CH_2CH_2CH_2$O— | A |
| HItz3' | G | —O—$CH_2CH_2CH_2$O— |
| HrbzL3.3 | —O—$CH_2CH_2CH_2$O— | —O—$CH_2CH_2CH_2$O— |
| HrbzL9 | —O—$(CH_2CH_2O)_3$— | A |
| HrbzL9' | G | —O—$(CH_2CH_2O)_3$— |
| HrbzL9.9 | —O—$(CH_2CH_2O)_3$— | —O—$(CH_2CH_2O)_3$— |
| HrbzL9.18 | —O—$(CH_2CH_2O)_3$— | —O—$(CH_2CH_2O)_6$— |
| HrbzL18.18 | —O—$(CH_2CH_2O)_6$— | —O—$(CH_2CH_2O)_6$— |

Several methods were used to insure that the products isolated were indeed monomer circles or circular hairpins. First, the mobility of the presumed circular and circular/hairpin products, in 15% denaturing polyacrylamide gels, was greater than that of their linear precursors. Second, the presumed circular and hairpin products could not be end-labeled with $^{32}$P-ATP and T4 polynucleotide kinase after treatment with alkaline phosphatase. In contrast, the linear precursors were efficiently labeled. Finally, the melting points of some of the circular/hairpin products were analyzed and found to be significantly increased over that of the linear precursors.

EXAMPLE 2
Cleavage Reactions

Cleavage reactions for circular and circular/hairpin ribozymes, and their linear counterpart, were performed in 10 μl and contained: 2.0 μM substrate (sub), 3.0 μM ribozyme, 50 mM Tris-HCl (pH 8.0), and 0.1% SDS, and were started with the addition of $MnCl_2$ to 25 mM. All reactions contained a trace of $^{32}$P-labeled sub for quantitation of Cleavage activity. Reactions were performed at room temperature for the times indicated. The reactions were stopped by adding 15 μl of stop mix (50 mM EDTA, 7M urea, 0.02% bromphenol blue, and 0.02% xylene cyanole) and run into 20% denaturing polyacrylamide gels. The gels were analyzed using a Molecular Dynamics Phosphorimager to determine the percentage cleaved.

Examination of cleavage reactions for linear contaminants. Circular ribozymes were incubated under similar conditions used in the cleavage reactions. Reaction conditions were as follows. One $\mu$M of ribozyme (containing a trace amount labeled with $^{32}$P) and 4.0 $\mu$M substrate (containing a trace amount labeled with $^{32}$P), alone or together, were incubated in 10 $\mu$l of cleavage buffer (50 mM Tris-HCl (pH 8.0), 20 mM MnCl$_2$, 0.1% SDS) at room temperature for 40 minutes. Subsequently the reactions were fractionated in a denaturing 20% polyacrylamide gel. The gel was visualized by autoradiography. Ribozymes and substrate were labeled with $^{32}$P using T4 polynucleotide kinase and $\gamma$-$^{32}$P ATP. For circular ribozymes, the linear precursors were labeled prior to circularization.

Cleavage activity of the circular ribozymes. For all cleavage reactions manganese chloride was used as the metal co-factor. The faster cleavage rates in the presence of manganese allowed reproducible cleavage activities to be obtained for even the slowest cleaving ribozyme variants. All of the circular ribozyme variants were able to specifically cleave the substrate strand, although their activities varied widely (FIG. 3A). The clCaYagC ativitid were low and comparable for the variants possessing linkers L0 through L9 (FIG. 3A). It is interesting that Crbzlx, which possessed a cytidine residue in place of a linker, exhibited activity slightly better than that of the linker L0 (no linker) to L9 variants. Cytidine is equivalent to L3 in terms of contour length, therefore it was expected that CrbzLc and CrbzL3 would possess similar activities.

In contrast to the variants with shorter linkers, CrbzL 18, CrbzL27, and CrbzL36 exhibited markedly better cleavage activity (FIG. 3A). In fact, CrbzL27 and CrbzL36 exhibited activity comparable to the linear ribozyme, Lrbz. The activity of CrbzL18 was only moderately educed relative to CrbzL27 and CrbzL36.

It can be argued that the cleavage activity of the circular ribozymes is due to contamination by the linear precursor. This is not likely for two reasons. First, the circular products were gel purified from the starting linear precursor. Second and more importantly, the linear precursors were not expected to possess catalytic activity, as the ligation point had been chosen such that the catalytic core was interrupted prior to ligation. The lack of cleavage activity of the linear precursor (pre-CrbzLc) was confirmed experimentally (FIG. 3A).

It is possible that the circular ribozymes may become nicked during the purification step or alternatively during the cleavage reaction. This is also an unlikely explanabon for the activity of the circular hammerheads. Because of their small size, the circular RNAs are not easily nicked in the experimental conditions, especially since all steps were performed at room temperature or lower. Even so, only a small percentage of nicked molecules are likely to be active, since nicks in the catalytic core or within the first 2 nucleotides in helices I and II should produce inactive ribozymes. It was also checked to see if linear contaminants could be observed in the cleavage reactions. For this, circular ribozymes were incubated under the same conditions used for the cleavage reactions and analyzed by denaturing polyacrylamide gel electrophoresis. This was performed using non-labeled, as well as, $^{32}$P-labeled circular ribozyme. No linear contamination was found by silver staining (non-labeled ribozyme) or autoradiography ($^{32}$P-labeled ribozyme, FIG. 3B). Finally, there was no difference in the level of linear contaminant for the different variants, even though their cleavage activities varied widely. Since the nucleotide sequence was the same for all variants, the same nick should produce the same catalytic activity for all variants. Therefore, nicking of the circular ribozymes cannot explain the cleavage activity, nor the differences in activity of the circular ribozymes. This was found to be true for the circular/hairpin ribozymes as well.

These findings suggest that there is a minimal distance needed to separate helices I and II to obtain optimal cleavage activity. This distance appears to be intermediate between the length of 27 and L36.

Cleavage activity of the circular/hairpin ribozymes. For comparison to the circular ribozymes, the circular/hairpin ribozymes were designed to be as similar as possible given the constraints of adding an additional hairpin connecting helices I and II (FIG. 2). For the wild-type hairpin ribozyme (Hrbz), X1 and X2 were G and A, respectively, to match the corresponding sequence for the circular ribozymes.

Similar to the circular ribozymes, all of the circular/hairpin ribozymes were able to cleave the substrate, again with widely varying activities (FIG. 4A). The variants with shorter linkers (L9 or shorter) exhibited low levels of activity, while the longer L18-containing variants possessed activities approaching that of the linear ribozyme.

The results of the L3 variants were interesting (FIG. 4A). The two single L3 variants, HrbzL3 and HrbzL3', exhibited cleavage activities comparable to that of the wild type Hrbz. In contrast, the double L3 variant, HibzL3.3, exhibited markedly reduced activity. It is not surprising that HrbzL3 and HrbzL3' would possess activities similar to the wild type, since the L3 linker approximated in length the single nucleotide it replaced. It was surprising that when both the A and G were replaced by L3 linkers (HrbzL3.3), the activity dropped significantly below that for the wild-type Hrbz.

The unexpected reduced activity of HrbzL3.3 was likely the consequence of the nucleotide composition closing helix IV. The wild type hairpin ribozyme was designed such that the closing base opposition was a G ($X_1$) and an A ($X_2$) on top of a C-G base pair. This motif was chosen because it is the same motif present at the top of the anticodon stem of yeast tRNAphe. In tRNAphe, this motif produces a noncanonical G-A pairing (propeller twist), which serves to widen the end of the anticodon stem and inhibit further stacking above (Sampson, J. R., DiRenzo, A. B., Behlen, L. S., and Uhlenbeck, O. C. (1990) Biochemistry 29, 2523–32). It is believed that this might be advantageous for the hairpin ribozymes.

In the context of the hairpin ribozyme, the G and A nucleotides can also participate in Watson-Crick pairings to helices I and II of the substrate. To determine how the G and A residues interact and influence cleavage activity, the cleavage activities of the hairpin ribozymes were examined against a different substrate, sub2 (SEQ ID NO:11). Sub2 had the same sequence as the wild-type substrate (sub) except that the 5' and 3' nucleotides were switched (see FIGS. 5A and C).

For cleavage of sub2 by the hairpin ribozyme variants, all cleavage activities were reduced in comparison to those for sub (FIG. 4B). This was likely the consequence of the inability of sub2 to form the two additional Watson-Crick base-pairs to Hrbz (and variants) as was possible for sub.

The relative activities of the L3 variants against sub2 differed from that observed for sub.

While HrbzL3 exhibited mildly reduced activity relative to Hrbz, HrbzL3' exhibited markedly enhanced activity.

Furthermore, HrbzL3.3 exhibited activity comparable, if not slightly better than Hrbz. Based on these findings, a simple model is described that explains the observed differences in activity of the L3 variants and the involvement of the G-A pair in affecting activity.

It is likely that the complex of sub/Hrbz can exist in equilibrium between two forms, A and B (FIG. 5A). In form A, the G-A pair participates in Watson-Crick pairing to the substrate, while for form B it participates in a non-canonical pairing within the ribozyme. Form B is expected to have a reduced cleavage activity relative to form A since the stability of the ribozyme/substrate complex is diminished with the loss of two interstrand base-pairs. This is supported by the reduced activities of all circular/hairpin ribozymes for sub2 versus sub.

The observed cleavage activity of sub by Hrbz represents the combined activities of the A and B form complexes. Replacement of G or A with L3 blocks the ability to form the non-canonical G-A pair and this produces a new complex A'. Complex A' is similar to complex A in that it lacks the G-A pairing, but it is dissimilar in that it can only form one of the two additional base-pairs possible for form A (FIGS. 5A and B). For sub, the comparable activities of Hrbz, HrbzL3 and HrbzL3' are likely due to the fact that the complexes with HrbzL3 and HrbzL3' will exist in the A' form. The A' form is expected to be intermediate in activity between the A and B forms. Since the cleavage activity of sub/Hrbz is likely due to the combined activities of A and B form complexes, it is not unreasonable to assume the combined activity would be comparable to the reduced activity of the A' form complexes of HrbzL3 and Hrbz3'. Additional support for this interpretation comes from the cleavage reactions using sub2 as substrate.

Similar to subA/Hrbz, the sub2/Hbz complex likely exists in equilibrium between two :4o forms. The two forms are likely to be an A'-like form, designated A", and a B form (FIG. 5C). The A" form is much like the A form of sub1Hrbz, except that only one of the two additional base-pairs is capable of forming, and it is a non-canonical G-U pair. The additional G-U pair is likely to enhance activity of the A" form over the B form.

For sub2 (FIG. 4B) the minor reduction in activity of HrbzL3, relative to Hrbz, is likely due to the loss of the U-G pairing in the A" complex. The increased activity of HrbzL3' is likely due to the elimination of the G-A pairing, which allows the ribozyme/substrate complex to xist solely in the more active A" form. The activity of HrbzL3.3 was expected to be similar to HrbzL3 since neither ribozyme is capable of forming the G-U base-pair. However, the mildly enhanced activity of HrizL3.3 relative to HrbzL3 (and Hrbz), might arise due to a favorable increase in conformational flexibility as a result of the dual L3 linkers.

Based on these findings, it appears that the non-canonical G-A pair itself does little to improve or inhibit cleavage activity. This is evident from the fact that the cleavage activities of HrbzL3, HrbzL3.3 and Hrbz against sub2 are fairly comparable. The two variants eliminate the G-A pairing without adding any additional base-pairs to helices I and II, while Hrbz likely exists predominately in the G-A paired B form. The diminished activity of HrbzL3.3 against sub and comparable activity against sub2, relative to Hrbz, reflects the difference in the number of base pairs forming helices I and II, for sub versus sub2. This suggests that the G-A pair influences cleavage activity only indirectly. If it is disrupted with a single linker, the opposing nucleotide can form an additional base-pair to the substrate to form a stronger ribozymetsubstrate complex, resulting in enhanced activity. If neither the G nor A nucleotides has the ability to base-pair to the substrate, replacement of one or the other with a linker has little effect on cleavage activity.

The cleavage activity of the L9 and L18 variants, in general, is improved over the L3 variants, with activity increasing with increasing linker length. The relative activities of these variants are similar for sub and sub2, with the overall activities greater for sub versus sub2 (FIGS. 4A and 4B). One striking result is the very low activity of HrbzL9 compared to HrbzL9'. In the crystal structures, the ends of helices I and II, next to the conserved core, are approximately even. Therefore, one might expect that asymmetrically increasing the distance between helix IV and helix I or II would be detrimental to the cleavage reaction. However, it is not clear why this asymmetry would affect position $X_1$ and not $X_2$.

Similar to the circular ribozymes, above a certain linker length the activity of circular/hairpin ribozymes approaches, or even exceeds, that of the linear ribozyme (FIGS. 4A and 4B). For HrbzL9.9, HrbzL9.18, and HrbzL18.18 the activities against sub were slightly lower than that of the linear ribozyme. For sub2, the same ribozymes possess activities comparable to, or even greater than, that of the linear ribozyme. This can be explained based on the differences in the number of base-pairs in which the ribozymes associate with the different substrates. HrbzL9.18 and HrbzL 18.18 can only associate with sub through a total of six base-pairs in helices I and II. For Lrbz, it can form 8 base-pairs to sub. For HxbzL9.18, HrbzL18.18, and Lrbz, all can associate with sub2 through only 6 base-pairs in helices I and II. Therefore, it is likely that the activities of HrbzL9.18 and HrbzL18.18 against sub would also exceed that of a suitably matched linear ribozyme.

EXAMPLE 3

Kinetic Analysis

The cleavage reactions were performed in 10 μl and contained 50 mM Tris-HCl (pH 8.0), 10 mM magnesium chloride, and 0.1% SDS to inhibit possible contaminating ribonucleases. The samples contained 20 nM ribozyme and up to 10 different concentrations of substrate ranging from 0.2–2.5 μM. A trace of $^{32}$P-labeled substrate was included to follow the extent of the reactions. All reaction mixtures were incubated at room temperatures for 30 minutes. The reactions were stopped by adding 10 μl of stop dye (80% formamide, 50 mM. EDTA, 0.2% bromphenol blue and xylene cyanole dyes), and run into 20% denaturing polyacrylamide gels. The gels were analyzed using a Molecular Dynamics Phosphorimager. Only data points in which the cleavage percentage was less than 20% were used to calculate the cleavage velocity. Km and kcat were determine by plotting at least six data points on an Eadie-Hofstee plot.

Kinetic Analysis of Circular Ribozymes. A minimal kinetic analysis has been performed on circular ribozymes possessing either the L18 or L27 linkers. To ensure that the results would be reliable, the circular ribozymes were based on a linear ribozyme characterized by Clouet, D. O. B., and Uhlenbeck, O. C. (1996) RNA 2,483–91. This ribozyme was shown to be homogeneous on non-denaturing gels, indicating that it does not exist in alternate inactive conformations. Additionally, it is well behaved kinetically. The linear and circular ribozymes use the same substrate, sub3 (SEQ ID NO:12), which associates with the ribozyme through five base-pairs in each of helices I and II (FIGS. 6A and 6B).

Michaelis-Menten constants were determined for the linear and circular ribozymes. The cleavage activities of the circular ribozymes, as reflected in the kcat values, were comparable to, or even greater than, that of the linear ribozyme (Table 3). The circular ribozymes exhibited only mildly reduced affinity for substrate than did the linear ribozyme, as reflected in the Km values. The Km for Crbz3L27 was somewhat improved over that of Crbz3L18. The specificity constants (kcat/Km) are similar for all three ribozymes.

TABLE 3

Kinetics of Cleavage of Sub3

| Ribozyme | kcat (min$^{-1}$) | Km ($\mu$M) | kcat/Km |
| --- | --- | --- | --- |
| Lrbz3 | 0.35 | 0.81 | 0.43 |
| Crbz3L18 | 0.30 | 2.2 | 0.14 |
| Crbz3L27 | 0.55 | 1.8 | 0.31 |

EXAMPLE 4

Magnesium Dependence of Cleavage

The magnesium dependence of cleavage of linear and circular ribozymes was examined under multi-turnover conditions. All reactions were performed in a final volume of 8 $\mu$l of water containing 50 mM Tris-HCl (pH 8.0) and 0.1% SDS. Substrate and ribozyme were added at a concentration of 4.0 $\mu$M and 50 nM, respectively. The reactions were started with the addition of magnesium chloride to differing concentrations. The reaction mixtures were incubated at room temperature for 30 minutes. The reactions were stopped by adding 380 $\mu$l of stopping solution (13 mM EDTA in 74% ethanol) and placing them at −20° C. for at least 1 hour to precipitate the RNA. The RNA was concentrated by centrifugation and electrophoresed into 20% denaturing PAGE gels, followed by quantitation using a Molecular Dynamics Phosphorimager.

The metal dependence of cleavage for Crbz3L18, Crbz3L27, and Lrbz3 were examined. The extent of cleavage was determined over a wide range of metal ion concentrations (FIG. 7). The metal dependence curves were similar for both circular ribozymes, with both leveling off above a concentration of approximately 200 mM. In contrast, there is no indication that the activity of the linear ribozyme will reach saturation, up to the highest concentration examined.

Crbz3L27 exhibited the highest activity of the three ribozymes, except at very high magnesium ion concentrations (i.e., above 700 mM; FIG. 7). At low magnesium ion concentration (i.e., below 50 mM, the activity of Crbz3L 27 was significantly better than that of Lrbz3 and Crbz3L18. For the linear ribozyme to achieve the same activity of Crbz3L27, in the range of 2 to 5 mM magnesium ion, a 1.5- to 10-fold higher concentration of magnesium was required. Since it has been estimated that the total intracellular magnesium ion concentration is in the range of 1 to 10 mM (Lehninger, A. L (1982) Principles of Biochemistry; Sperealakis, N., (1995) Cell Physiology Source Book), the much higher activity of Crbz3L27, at low magnesium ion concentrations, may offer significant advantage for antisense use.

The apparent saturation of the magnesium dependence curves of the circular ribozymes can likely be explained in terms of the equilibrium between an open and closed conformation (FIG. 1A). Both ribozymes, by virtue of their linkers, exist in a conformation approaching that of the fully closed and active ribozyme. Therefore, much lower magnesium ion concentrations are needed to further shift the equilibrium towards the fully active closed conformation. Furthermore, above a certain concentration (i.e., 200 mM), no additional stabilization is gained. In contrast, the closed conformation of the linear ribozyme is likely to be very unfavorable due to charge repulsion between helices I and II. In this case, increasing magnesium ion concentrations continue to shift the equilibrium toward the closed conformation, up to the highest concentrations examined.

It is interesting that although both circular ribozymes appear to be saturated at approximately the same magnesium ion concentration, their levels of activity at saturation are quite different. This suggests that both circular ribozymes have a reduced dependence on magnesium ion, compared to the linear ribozyme, at least in terms of structure. The difference in maximal activity of the circular ribozymes simply reflects a difference in their catalytic efficiencies. This difference in efficiency may be the result of the L18 linker being too short for optimal separation of helices I and II, causing the catalytic core of Crbz3L18 to be less optimally folded relative to Crbz3L27. This is supported by the results with the Crbz linker variants (FIG. 3A).

The linkers in covalently closed hammerhead ribozymes are likely to influence activity in a number of ways. The linker can influence activity by determining the distance separating helices I and II. In this regard, the low activity of the shorter linker containing circles and a hairpins may be attributed to a less than optimal separation of helices I and II. In this case, the longer linker containing ribozymes appear to possess a more optimal separation. However, the separation that the longer linkers allow appears to be greater than that needed. For instance, in the crystal structures, helices I and II are separated by approximately 25 Å. For the circular and hairpin ribozymes to exhibit activity comparable to the linear ribozyme, linker lengths of 45 Å (CrbzL36) and 37 Å (HrbzL9.9, includes the diameter of helix IV) appear to be necessary. This might suggest, that in addition to influencing activity by affecting the separation of helices I and II, the linkers may affect activity in another manner.

On binding of substrate to ribozyme, the action of forming helices I and II causes twisting or supercoiling of the covalently closed ribozymes. This induced twist could enhance or diminish activity. Most likely, the induced twist is detrimental to the cleavage activity as it can perturb the structure of the catalytic core. As longer linkers have greater conformational flexibility, they are more capable of relaxing the supercoiling by absorbing the twist. This could in part explain the trend toward increasing activity with increasing linker length. This could also explain why covalently closed ribozymes require linkers significantly greater than 25 Å in length to obtain activity comparable to the linear ribozyme. In this case, the shorter linkers may provide a more optimal separation of helices I and II. However, since they are less able to relieve induced twist, they produce a less active ribozyme.

Induced twist may influence activity in multiple ways. It may perturb the structure of the catalytic core to produce a less active ribozyme. This possibility is supported by the observed increase in activity with increasing linker length for the circular and circular/hairpin ribozymes. This is also supported by the faster kcat for Crbz3L27 relative to CrbzL8.

In addition to perturbing the structure of the catalytic core, induced twist may influence substrate binding (and/or product release). Support for this is the observed higher Km values for Crbz3L18 and Crbz3L27 relative to Lrbz3 and the lower Km for Crbz3L27 relative to Crbz3L18.

If twist absorption is an important function of the linkers, then circularized ribozymes possessing longer helices I and II will likely require even longer linkers to exhibit activity comparable to the analogous linear ribozyme.

These studies demonstrate that hammerhead ribozymes of the I/II format can be covalently closed into circles or circular/hairpins, and retain catalytic activity. The examination of constructs containing varying linker lengths has allowed elucidation of some of the factors that can influence activity of covalently closed ribozymes. In this manner it has been possible to produce circular and circular/hairpin ribozymes possessing activity approaching and even exceeding that of their linear counterparts.

Since these novel configurations constrain the hammerhead ribozyme into a closed (and likely, more active) conformation, they may prove to be useful alternatives for structure function studies. Additionally, these covalently closed ribozymes are useful as antisense therapeutics. They provide advantages of increased activity, reduced metal ion requirements, and greater resistance to nucleases. Although they suffer the disadvantage of placing greater constraints on the possible sequences that can be targeted, compared to IYM format ribozymes typically used, an examination of Genbank reveals that targets can be readily found.

Illustrative circular, hairpin, circular/hairpin, lariat, and hairpin-lariat configured hammerhead ribozymes are shown in FIGS. 8B–D and 8F–G. Also shown are the corresponding wild type III (FIG. 8A) and I/III (FIG. 8E) ribozymes. For clarity, only the wild-type ribozymes are shown with their substrate molecules. All five of the new ribozyme configurations have been shown to possess cleavage activity. The following notes relate to FIGS. 8A–G.

Helices I, II, III, and IV are as indicated. The lengths of the four helices can be varied as needed. There are no upper limits other than functionality on the length of the helices, but 2–3 base-pairs appears to be the practical lower limit. The stems can be closed with a loop. Again there is no upper limit other than functionality on the size of the loops, but loops of 3 to 4 nucleotides seem optimal. Since zero, one, two, or three of the stems, in any combination, can be closed by loops, there is great flexibility in how the hammerhead can beconstructed. L represents a linker. The linker can be composed of zero (i.e. direct connection) or 1 or more nucleotide residues. Alternatively, L can be composed of non-nucleotide linkers of varying length, such as, but not limited to, Spacer Phosphoramidites C3, 9, and 18 (Glenn Research, #10-1913, 10-1909, or 10-1918, respectively). $X_1$, $X_2$, and Z represent linkers. The composition of these linkers is defined by the L linker. $X_1$ and $X_2$ may or may not be the same composition and length. Y is a linker and its composition is defined by the L linker. In terms of being a linker composed of nucleotides, it would likely be composed of one of the highly stable tetraloops, such as the gnra or uncg tetraloops (n=any nucleotide and r=a purine nucleotide). B is a branched connection. The branch point can be placed at the end of the helix II as illustrated, but also within helix II. In either case, the branch could be produced using an asymmetric branching phosphoramidite (Clontech #5252, Palo Alto, Calif.). Alternatively, the branch can be introduced using modified nucleotides possesing a pendant functional group on the base or sugar, such as, but not limited to, Carboxy-dT (Glenn Research, #10-1035-90). The pendant functional group is used to couple the linker to form the branched structure.

Circularization of the circular, circular/hairpin, and lariat ribozymes can be achieved in a variety of ways. It can be achieved enzymatically using DNA or RNA ligase, both of which are commercially available from several sources. It can be achieved with any number of chemical methods. Circularization typically would be performed after chemical synthesis of the precursor RNA molecules and could use both chemical and enzymatic means. It is also possible to perform the circularization during automated synthesis on a DNA synthesizer using the dT Nucleotide PS support (Glenn Research, #26-2630).

As used herein, "oligonucleotide" or "oligoribonucleotide" have no particular intended size limitation, unless a particular size is otherwise stated

We claim:

1. A hammerhead ribozyme derivative having a structure represented by:

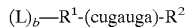

wherein $R^1$ and $R^2$ are oligoribonucleotides of at least 2 bases configured for base pairing with a substrate; L is a spacer, and b is 0 or 1, with the proviso that if b is 0, then $R^1$ and $R^2$ are bonded together with a phosphodiester bond, and if b is 1, then L is bonded to $R^2$.

2. The hammerhead ribozyme derivative of claim 1 wherein L is at least one ribonucleotide residue.

3. The hammerhead ribozyme derivative of claim 1 wherein L is a member selected from the group consisting of —O—CH$_2$CH$_2$CH$_2$O—, —O—(CH$_2$CH$_2$O)$_3$—, —O—(CH$_2$CH$_2$O)$_6$—, —O—(CH$_2$CH$_2$O)$_3$—OPO$_3$—O—(CH$_2$CH$_2$O)$_6$—, and —O—(CH$_2$CH$_2$O)$_6$—OPO$_3$—O—(CH$_2$CH$_2$O)$_6$—.

4. A hammerhead ribozyme derivative having a structure represented by:

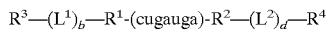

wherein $R^1$ and $R^2$ are oligoribonucleotides of at least 2 bases configured for base pairing with a substrate; $R^3$ and $R^4$ are oligonucleotides of at least 2 bases configured for base pairing with each other, $L^1$ and $L^2$ are spacers; and b and d are 0 or 1.

5. The hammerhead ribozyme derivative of claim 4 wherein b and d are 0.

6. The hammerhead ribozyme derivative of claim 4 wherein b and d are 1, and $L^1$ and $L^2$ are independently selected from the group consisting of ribonucleotides and oligoribonucleotides.

7. The hammerhead ribozyme derivative of claim 4 wherein b and d are 1, and $L^1$ and $L^2$ are independently selected from the group consisting of —O—CH$_2$CH$_2$CH$_2$O—, —O—(CH$_2$CH$_2$O)$_3$—, —O—(CH$_2$CH$_2$O)$_6$—, —O—(CH$_2$CH$_2$O)$_3$—OPO$_3$—O—(CH$_2$CH$_2$O)$_6$—, and —O—(CH$_2$CH$_2$O)$_6$—OPO$_3$—O—(CH$_2$CH$_2$O)$_6$—.

8. A hammerhead ribozyme derivative having a structure represented by:

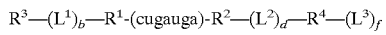

wherein $R^1$ and $R^2$ are oligoribonucleotides of at least 2 bases configured for base pairing with a substrate; $R^3$ and $R^4$ are oligonucleotides of at least 2 bases configured for base pairing with each other; $L^1$, $L^2$, and $L^3$ are spacers; and b, d, and f are 0 or 1, with the proviso that if f is 0, then $R^3$ and $R^4$ are bonded together by a phosphodiester bond, and if f is 1, then $L^3$ is bonded to both $R^3$ and $R^4$.

9. The hammerhead ribozyme derivative of claim 8 wherein b and d are 0.

10. The hammerhead ribozyme derivative of claim 8 wherein b and d are 1, and $L^1$ and $L^2$ are independently selected from the group consisting of ribonucleotides and oligoribonucleotides.

11. The hammerhead ribozyme derivative of claim 8 wherein b and d are 1, and $L^1$ and $L^2$ are independently selected from the group consisting of —O—CH$_2$CH$_2$CH$_2$O—, —O—(CH$_2$CH$_2$O)$_3$—, —O—(CH$_2$CH$_2$O)$_6$—, —O—(CH$_2$CH$_2$O)$_3$—OPO$_3$—O—(CH$_2$CH$_2$O)$_6$—, and —O—(CH$_2$CH$_2$O)$_6$—OPO$_3$—O—(CH$_2$CH$_2$O)$_6$—.

12. The hammerhead ribozyme derivative of claim 8 wherein f is 0.

13. The hammerhead ribozyme derivative of claim 8 wherein f is 1, and $L^3$ is a member selected from the group consisting of ribonucleotides, oligoribonucleotides, —O—CH$_2$CH$_2$CH$_2$O—, —O—(CH$_2$CH$_2$O)$_3$—, —O—(CH$_2$CH$_2$O)$_6$—, —O—(CH$_2$CH$_2$O)$_3$—OPO$_3$—O—(CH$_2$CH$_2$O)$_6$—, and —O—(CH$_2$CH$_2$O$_6$—OPO$_3$—O—(CH$_2$CH$_2$O)$_6$—.

14. A hammerhead ribozyme derivative having a structure represented by:

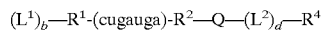

wherein $R^1$ is an oligoribonucleotide of at least 2 bases configured for base pairing with a substrate; $R^2$ is an oligoribonucleotide of at least 2 bases configured for base pairing with $R^4$; $R^4$ is an oligonucleotide of at least 2 bases configured for base pairing with $R^2$; $L^1$ and $L^2$ are spacers; Q is a branching moiety; and b and d are 0 or 1, with the proviso that is b is 0, then $R^1$ is covalently bonded to Q, and if b is 1, then $L^1$ is covalently bonded to Q.

15. The hammerhead ribozyme derivative of claim 14 wherein b and d are 0.

16. The hammerhead ribozyme derivative of claim 14 wherein b and d are 1, and $L^1$ and $L^2$ are independently selected from the group consisting of ribonucleotides, oligoribonucleotides, —O—CH$_2$CH$_2$CH$_2$O—, —O—(CH$_2$CH$_2$O)$_3$—, —O—(CH$_2$CH$_2$O)$_6$—, —O—(CH$_2$CH$_2$O)$_3$—OPO$_3$—O—(CH$_2$CH$_2$O)$_6$—, and —O—(CH$_2$CH$_2$O)$_6$—OPO$_3$—O—(CH$_2$CH$_2$O)$_6$—.

17. A hammerhead ribozyme derivative having a structure represented by:

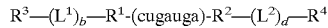

wherein $R^1$ is an oligoribonucleotide of at least 2 bases configured for base pairing with a substrate; $R^2$ is an oligoribonucleotide of at least 2 bases configured for base pairing with both $R^3$ and $R^4$; $R^3$ is an oligonucleotide of at least 2 bases configured for base pairing with $R^2$; $L^1$ and $L^2$ are spacers; and b and d are 0 or 1.

18. The hammerhead ribozyme derivative of claim 17 wherein b and d are 0.

19. The hammerhead ribozyme derivative of claim 17 wherein b and d are 1, and $L^1$ and $L^2$ are independently selected from the group consisting of ribonucleotides, oligoribonucleotides, —O—CH$_2$CH$_2$CH$_2$O—, —O—(CH$_2$CH$_2$O)$_3$—, —O—(CH$_2$CH$_2$O)$_6$—, —O—(CH$_2$CH$_2$O)$_3$—OPO$_3$—O—(CH$_2$CH$_2$O)$_6$—, and —O—(CH$_2$CH$_2$O)$_6$—OPO$_3$—O—(CH$_2$CH$_2$O)$_6$—.

* * * * *

SEQUENCE LISTING

```
<160> NUMBER OF SEQ ID NOS: 20

<210> SEQ ID NO 1
<211> LENGTH: 22
<212> TYPE: RNA
<213> ORGANISM: Artificial Sequence
<220> FEATURE:
<223> OTHER INFORMATION: Substrate (sub) for hammerhead ribozymes.

<400> SEQUENCE: 1
cgccgaaacg guaacgucuc gu                                          22

<210> SEQ ID NO 2
<211> LENGTH: 15
<212> TYPE: RNA
<213> ORGANISM: Unknown
<220> FEATURE:
<223> OTHER INFORMATION: Linear hammerhead ribozyme (Lrbz) and circular
      hammerhead ribozyme (Crbz).

<400> SEQUENCE: 2
acgacugaug aggcg                                                  15

<210> SEQ ID NO 3
<211> LENGTH: 16
```

```
<212> TYPE: RNA
<213> ORGANISM: Artificial Sequence
<220> FEATURE:
<223> OTHER INFORMATION: Circular hammerhead ribozyme (CrbzLc).

<400> SEQUENCE: 3
acgacugaug aggcgc                                                    16

<210> SEQ ID NO 4
<211> LENGTH: 33
<212> TYPE: RNA
<213> ORGANISM: Artificial Sequence
<220> FEATURE:
<223> OTHER INFORMATION: Circular/hairpin hammerhead ribozyme (Hrbz).

<400> SEQUENCE: 4
cgacugauga ggcgcucgaa ggaaacuucg aga                                 33

<210> SEQ ID NO 5
<211> LENGTH: 32
<212> TYPE: RNA
<213> ORGANISM: Artificial Sequence
<220> FEATURE:
<223> OTHER INFORMATION: Circular/hairpin hammerhead ribozymes (HrbzL3
      and HrbzL9).

<400> SEQUENCE: 5
cucgaaggaa acuucgagac gacugaugag gc                                  32

<210> SEQ ID NO 6
<211> LENGTH: 32
<212> TYPE: RNA
<213> ORGANISM: Artificial Sequence
<220> FEATURE:
<223> OTHER INFORMATION: Circular/hairpin hammerhead ribozymes (HrbzL3
      and HrbzL9 ).

<400> SEQUENCE: 6
cgacugauga ggcgcucgaa ggaaacuucg ag                                  32

<210> SEQ ID NO 7
<211> LENGTH: 13
<212> TYPE: RNA
<213> ORGANISM: Artificial Sequence
<220> FEATURE:
<223> OTHER INFORMATION: Circular portion of circular/hairpin hammerhead
      ribozymes.

<400> SEQUENCE: 7
cgacugauga ggc                                                       13

<210> SEQ ID NO 8
<211> LENGTH: 18
<212> TYPE: RNA
<213> ORGANISM: Artificial Sequence
<220> FEATURE:
<223> OTHER INFORMATION: Hairpin portion of circular/hairpin hammerhead
      ribozymes.

<400> SEQUENCE: 8
cucgaaggaa acuucgag                                                  18

<210> SEQ ID NO 9
<211> LENGTH: 15
<212> TYPE: RNA
<213> ORGANISM: Artificial Sequence
<220> FEATURE:
```

```
<223> OTHER INFORMATION: Precursor of Crbz.

<400> SEQUENCE: 9
augaggcgac gacug                                                    15

<210> SEQ ID NO 10
<211> LENGTH: 33
<212> TYPE: RNA
<213> ORGANISM: Artificial Sequence
<220> FEATURE:
<223> OTHER INFORMATION: Precursor of Hrbz.

<400> SEQUENCE: 10
augaggcgcu cgaaggaaac uucgagacga cug                                33

<210> SEQ ID NO 11
<211> LENGTH: 22
<212> TYPE: RNA
<213> ORGANISM: Artificial Sequence
<220> FEATURE:
<223> OTHER INFORMATION: Substrate (sub2) for hammerhead ribozymes.

<400> SEQUENCE: 11
ugccgaaacg guaacgucuc gc                                            22

<210> SEQ ID NO 12
<211> LENGTH: 26
<212> TYPE: RNA
<213> ORGANISM: Artificial Sequence
<220> FEATURE:
<223> OTHER INFORMATION: Substrate (sub3) for hammerhead ribozymes.

<400> SEQUENCE: 12
gaaucgaaac gcgaaagcgu cggucg                                        26

<210> SEQ ID NO 13
<211> LENGTH: 17
<212> TYPE: RNA
<213> ORGANISM: Unknown
<220> FEATURE:
<221> NAME/KEY: misc RNA
<222> LOCATION: 1-5 and 13-17
<223> OTHER INFORMATION: Wild-type I/II ribozyme.

<400> SEQUENCE: 13
nnnnncugau gannnnn                                                  17

<210> SEQ ID NO 14
<211> LENGTH: 26
<212> TYPE: RNA
<213> ORGANISM: Artificial Sequence
<220> FEATURE:
<221> NAME/KEY: misc RNA
<222> LOCATION: 1-5 and 22-26
<223> OTHER INFORMATION: Substrate for wild type I/II hammerhead
      ribozymes.

<400> SEQUENCE: 14
nnnnngaaac gcgaaagcgu cnnnnn                                        26

<210> SEQ ID NO 15
<211> LENGTH: 33
<212> TYPE: RNA
<213> ORGANISM: Artificial Sequence
<220> FEATURE:
<221> NAME/KEY: misc RNA
<222> LOCATION: 1-4 and 28-33
```

<223> OTHER INFORMATION: Wild-type I/III ribozyme

<400> SEQUENCE: 15
nnnncugaug agcucgaaag agcgaaannn nnn                         33

<210> SEQ ID NO 16
<211> LENGTH: 12
<212> TYPE: RNA
<213> ORGANISM: Artificial Sequence
<220> FEATURE:
<221> NAME/KEY: misc RNA
<222> LOCATION: 1-6 and 9-12
<223> OTHER INFORMATION: Substrate for wild-type I/III hammerhead
      ribozymes.

<400> SEQUENCE: 16
nnnnnnuhnn nn                                                12

<210> SEQ ID NO 17
<211> LENGTH: 19
<212> TYPE: RNA
<213> ORGANISM: Artificial Sequence
<220> FEATURE:
<221> NAME/KEY: misc RNA
<222> LOCATION: 1-4
<223> OTHER INFORMATION: Portion of hairpin/lariate ribozyme.

<400> SEQUENCE: 17
nnnncugaug agcuccgag                                         19

<210> SEQ ID NO 18
<211> LENGTH: 14
<212> TYPE: RNA
<213> ORGANISM: Artificial Sequence
<220> FEATURE:
<221> NAME/KEY: misc RNA
<222> LOCATION: 9-14
<223> OTHER INFORMATION: Portion of hairpin/lariate ribozyme.

<400> SEQUENCE: 18
gagcgaaann nnnn                                              14

<210> SEQ ID NO 19
<211> LENGTH: 32
<212> TYPE: DNA
<213> ORGANISM: Artificial Sequence
<220> FEATURE:
<223> OTHER INFORMATION: Guide for synthesis of CrbzLc.

<400> SEQUENCE: 19
gtcgctaaga cacgtgcgcc acacttagcg ac                          32

<210> SEQ ID NO 20
<211> LENGTH: 31
<212> TYPE: DNA
<213> ORGANISM: Artificial Sequence
<220> FEATURE:
<223> OTHER INFORMATION: Guide for synthesis of CrbzL0.

<400> SEQUENCE: 20
gtcgctaaga cacgtcgcca cacttagcga c                           31